US008903786B2

(12) United States Patent
Kottaram (10) Patent No.: US 8,903,786 B2
(45) Date of Patent: Dec. 2, 2014

(54) INTELLIGENT RESOLUTION OF CODES IN A CLASSIFICATION SYSTEM (71) Applicant: International Business Machines Corporation, Armonk, NY (US)

(72) Inventor: Sanjay F. Kottaram, Cedar Park, TX (US)

(73) Assignee: International Business Machines Corporation, Armonk, NY (US)

(*) Notice: Subject to any disclaimer, the term of this patent is extended or adjusted under 35 U.S.C. 154(b) by 19 days.

(21) Appl. No.: 13/677,691

(22) Filed: Nov. 15, 2012

(65) Prior Publication Data

US 2014/0136495 A1   May 15, 2014

(51) Int. Cl.
G06F 7/00       (2006.01)
G06F 17/00      (2006.01)

(52) U.S. Cl.
USPC ............................ 707/695; 707/756; 707/759

(58) Field of Classification Search
CPC ....... G06Q 50/22; G06Q 50/24; G06Q 10/00; G06F 19/3487; G06F 19/321
USPC ........................................................ 707/695
See application file for complete search history.

(56) References Cited

U.S. PATENT DOCUMENTS

| 2004/0249667 | A1 | 12/2004 | Oon | |
|2006/0218538|A1*|9/2006|van Kesteren|717/137|
|2010/0088117|A1*|4/2010|Belden et al.|705/3|
|2010/0114607|A1*|5/2010|Kress et al.|705/3|
|2012/0254083|A1*|10/2012|Patrao et al.|706/14|
|2013/0035947|A1*|2/2013|Sundararam et al.|705/2|
|2013/0073301|A1*|3/2013|Rao et al.|705/2|
|2013/0144651|A1*|6/2013|Rao|705/3|

FOREIGN PATENT DOCUMENTS

WO      2012058242 A2    5/2012

* cited by examiner

Primary Examiner — Binh V Ho
(74) Attorney, Agent, or Firm — Cantor Colburn LLP; Parashos Kalaitzis (57) ABSTRACT Intelligent delegation of codes for mapping between versions of a classification system includes a computer processor and an application executable by the computer processor to implement a method. The method includes receiving data that is classified with a first code. The first code is defined by a first version of the classification system, and the first code is to be re-classified to a second code that is defined by a second version of the classification system. The method also includes searching a database of profiles for content that matches at least a portion of the data, sending the data to a converter system having one of the profiles that is associated with the content responsive to the searching, and receiving, from the converter system, a mapping of the first code to the second code. The method further includes updating a database of codes with results of the mapping.

11 Claims, 5 Drawing Sheets

| User Profile Model / Train | Capability 1 | Capability 2 | Capability 3 | .... | Capability N | Diagnostic Category |
|---|---|---|---|---|---|---|
| User1 | 0.5 | 0.65 | 0 | | | D1 |
| User1 | 0.25 | 0.33 | 0.4 | | | D2 |
| User1 | | | | | | D3 |
| User1 | | | | | | ... |
| : | | | | | | ... |
| : | | | | | | ... |
| User n | | | | | | D n |

# INTELLIGENT RESOLUTION OF CODES IN A CLASSIFICATION SYSTEM

BACKGROUND

The present invention relates to data processing and, more specifically, to intelligent resolution of codes in a classification system.

Code mapping is generally a manual process in which one or more individuals are tasked with associating codes defined by one version of a classification system to codes defined by a different version of the classification system, or alternatively, converting codes between two different classification systems. One example of a classification system is the International Classification of Diseases (ICD), which is an international standard diagnostic classification system for epidemiological use, as well as health management and clinical use purposes. This classification system has been recently updated from version 9 (ICD-9) to version 10 (ICD-10).

Migrating between classification systems or between versions of any classification system can be time consuming and error prone, particularly when the data used in the mapping process is ambiguous. Using the ICD example above, there are multiple structural changes and exponential increases in the number and possible combinations of codes between version ICD-9 and version ICD-10. For example, version ICD-9 employs approximately 18,000 diagnostic and procedure codes, while version ICD-10 employs about 141,000 diagnostic and procedure codes. This increase in the number of codes is due, in part, to the level of detail added in the ICD-10 version with respect to clinical descriptions of signs, symptoms, conditions, and procedures.

SUMMARY

According to another embodiment of the present invention, a system is provided. The system includes a computer processor and an application executable by the computer processor. The application is configured to implement a method. The method includes receiving data that is classified with a first code. The first code is defined by a first version of a classification system, and the first code is to be re-classified to a second code that is defined by a second version of the classification system. The method also includes searching a database of profiles for content that matches at least a portion of the data, sending the data to a converter system having one of the profiles that is associated with the content responsive to the searching, and receiving, from the converter system, a mapping of the first code to the second code. The method further includes updating a database of codes with results of the mapping.

According to a further embodiment of the present invention, a computer program product is provided. The computer program product includes a storage medium embodied with instructions, which when executed by a computer processor, causes the computer processor to implement a method. The method includes receiving, by a computer processor, data that is classified with a first code. The first code is defined by a first version of a classification system, and the first code is to be re-classified to a second code that is defined by a second version of the classification system. The method also includes searching a database of profiles for content that matches at least a portion of the data, sending the data to a converter system having one of the profiles that is associated with the content responsive to the searching, and receiving, from the converter system, a mapping of the first code to the second code. The method further includes updating, by the computer processor, a database of codes with results of the mapping.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

In an exemplary embodiment, intelligent resolution of codes in a classification system is provided. The intelligent resolution of codes includes a process for training a data processing system to evaluate incoming data associated with a code and for determining a mapping between versions of the classification system with respect to the code. When a code is unresolved by the data processing system (i.e., no mapping or association between codes of the two versions is determined), the process includes identifying a profile that is related to the data and submitting the data to an individual associated with the profile for resolution of the code.

In addition, mapping activities performed by individuals associated with various profiles are monitored and analyzed to determine a proficiency level of each of the individuals with respect to a particular subject area or body of information. Individuals determined to be proficient in a particular subject area are then targeted for performing resolution of codes associated with new data that fall within the particular subject area. A database is updated to reflect results of the mapping processes, such that future incoming data relating to the subject area may be quickly and efficiently resolved using the trained system. These and other features of the intelligent resolution of codes for a classification system will now be described.

Figure 1:
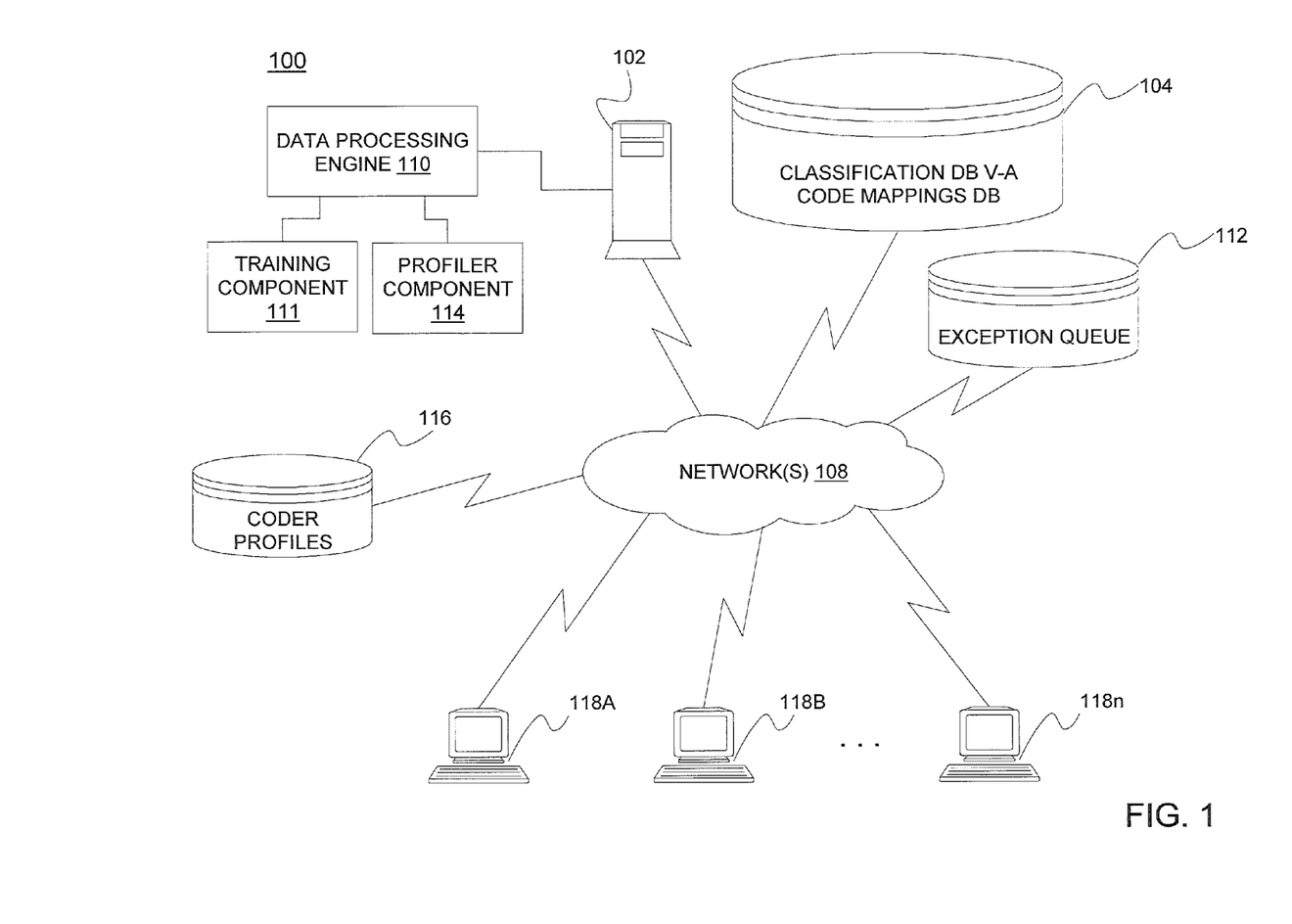
FIG. 1 is a block diagram depicting a system upon which intelligent resolution of codes for a classification system may be implemented in accordance with an embodiment.

With reference now to FIG. 1, a data processing system 100 (also referred to herein as "system") upon which embodiments of the invention may be implemented will now be described. The system 100 includes a host system computer 102, storage devices 104, 112, and 116, and converter systems 118A-118n, each of which is communicatively coupled to one or more network(s) 108.

For purposes of illustration, the embodiments are described herein with respect to medical insurance claim processing and adjudication. In these embodiments, an entity operating the host system computer 102 may be an insurance company, and data may be received by the host system computer 102 as claim forms submitted by health care providers servicing patients that subscribe to a health plan managed by the insurance company. When a revised classification system for coding medical information used in the claim forms has been issued, the system 100 attempts to resolve codes found in incoming claim forms, which claim forms comply with one version of the classification system, with codes used by the other version of the classification system. In an embodiment, the code is defined by a standards authority, such as the authority responsible for the International Classification of Diseases. Claim forms having unresolved codes are placed in a queue for resolution by selected coders, as will be described herein.

While the embodiments described herein relate to the insurance industry, the invention is not so limited. For example, the intelligent resolution of codes may be employed in any industry using a classification system of codes to process data.

The host system computer 102 of FIG. 1 may be implemented as a high-speed computer processing system (e.g., one or more server computers operating in response to a computer program stored in a storage medium accessible by the server computers). Data may be received by the host system computer 102 as claim forms submitted by health care providers. The claim forms may include patient information, as well as diagnostic and/or procedure codes and related information associated with the patients. The claims forms may also include fees charged for services rendered by the health care provider. In an embodiment, the claim forms are ICD-10 compliant; however, the host system computer 102 operates software configured to process claim forms recognized by version ICD-9.

The storage devices 104, 112, and 116 may be implemented using a variety of devices for storing electronic information. It is understood that the storage devices 104, 112, and 116 may be implemented using memory contained in the host system computer 102 or may be separate physical devices, as shown in FIG. 1 for illustrative purposes. The storage devices 104, 112, and 116 may be logically addressable as consolidated data sources across a distributed environment that includes the network(s) 108. Information stored in the storage devices 104, 112, and 116 may be retrieved and manipulated via the host system computer 102 and other systems authorized by the host system computer 102.

In an embodiment, the storage device 104 stores databases including a database of codes and associated information for one version of a classification system (referred to as version A or "V-A") that is used by the host system computer 102. The host system computer 102 processes claim forms that are compliant with another version of the classification system (referred to as version B or "V-B"). The first version (V-A) reflects the version currently used by the entity operating the host system computer 102 and the V-A database stores ICD-9 compliant codes.

The storage device 104 also stores a code mappings database. In an embodiment, the code mappings database stores results of code mappings performed by the system, as well as those performed by coders associated with the system. A code mapping process includes identifying a closest (or most relevant) relationship between data associated with a code defined by one version of a classification system and data associated with a code defined by a different version of the classification system. Once the relationship is identified, the code of the first version is mapped to the code of the second version, and results of the mapping are stored in the code mappings database in the storage device 104.

In an embodiment, the storage device 112 stores claim forms having unresolved codes in an exception queue for processing. For example, claim forms for which no clear mapping between codes can be determined may be stored in the exception queue, as described further herein.

In an embodiment, the storage device 116 stores coder profiles. A profile may include identifying information regarding a coder, as well as the coder's capabilities with respect to previously-conducted and ongoing coding activities. In addition, the profile may include one or more subject areas in which the coder has performed coding activities. In an embodiment, the profile includes identifiers of one or more subject matter areas in which the coder is deemed proficient in terms of the performance of coding activities. Those coders determined to be highly proficient with a particular subject matter may be assigned future claim forms relating to the subject matter, which have unresolved codes. The term, coder, refers to an individual who is tasked with performing the mapping of codes between versions of a classification system when the system is unable to do so. Profiles are created for these coders and are used to monitor coder activities with respect to code mappings, as well as assign incoming data related to unresolved claims to selected coders. A profile 600 is shown and described further in FIG. 6.

The converter systems 118A-118n may be implemented using general-purpose computers executing computer programs for carrying out some of the processes described herein. The converter systems 118A-118n may be personal computers (e.g., desktops, lap tops, personal digital assistants, tablet computers, etc.) or host-attached terminals. Individuals who process claims having unresolved codes are referred to as coders, and these coders operate respective converter systems 118A-118n.

Network(s) 108 may include any types of known networks including, but not limited to, a wide area network (WAN), a local area network (LAN), a global network (e.g. Internet), a virtual private network (VPN), and an intranet. The network (s) 108 may be implemented using wireless technologies or any kind of physical network implementation known in the art. One or more of the converter systems 118A-118B and the host system computer 102 may be coupled to one another through multiple networks (e.g., intranet and Internet) 108 so that not all systems are coupled to one another through the same network. One or more of the converter systems 118A-118B and the host system computer 102 may be connected to the network(s) 108 in a wireless fashion.

The host system computer 102 executes a data processing engine 110 for handling incoming data received by the entity of the host system computer 102. As indicated above, the data may include claim forms received from health care providers or patients who seek reimbursement or payment of health care services. The data may include a description of a diagnosis, a medical procedure or service, an amount of time spent by a patient in a hospital or clinic, and a fee charged for the service or procedure, to name a few. The data also includes a code that is associated with the diagnosis and/or procedure.

When a new or revised classification system is generated by an authority, such as the ICD, the entity (e.g., insurance company) may need to convert or map the codes between the two versions of the classification system in order to process the claim forms and report processing activities to governmental agencies that regulate the insurance company (e.g., Centers for Medicare & Medicaid Services). As indicated above, an index of these codes prior to the mapping process is stored in the storage device 104 in a classification database (e.g., classification database V-A). The data processing engine 110 attempts to resolve the codes in the claim forms to the other version of the classification system by a training component 111 of the data processing engine 110 and, if unable, the claim forms are sent to an exception queue stored in the storage device 112. Claim forms having unresolved codes in the exception queue are then handled by experienced coders via the converter systems 118A-118n, as will be described herein. Once a code for a given claim form has been resolved, the data processing engine 110 processes the claim for payment.

In an embodiment, the training component 111 of the data processing engine 110 analyzes features or characteristics of data from incoming claim forms, such as a set of symptoms, treatment performed, how much time a patient spent at a clinic or hospital, etc., and attempts to resolve a code identified in the claim form to another code used by a different version of the classification system. The training component 111 may apply a score or relevance value to each feature based on how relevant the feature is to the features or characteristics identified for a code of the other version of the classification system. An overall high score indicates that features identified for a code in the other version of the classification system closely match those found in the claim form. A model 400 used by the training component 111 is shown and described in FIG. 4.

The training component 111 updates the code mappings database via the data processing engine 110 with a mapping between the code from the claim form and the code from the other version. The training component 111 learns over time to identify code mappings as it processes new claim forms. If the training component 111 is unable to identify a code from the second version of the classification system, the claim form is placed in the exception queue, as described further herein.

A profiler component 114 of the data processing engine 110 creates and maintains profiles for use in handling unresolved codes sent to the exception queue. The profiles, once created, are stored in the storage device 116. The profiler component 114 also monitors coder activities with respect to mapping processes, rates the respective coders, and assigns subject areas of expertise to these coders based on a history of past performance.

Figure 2:
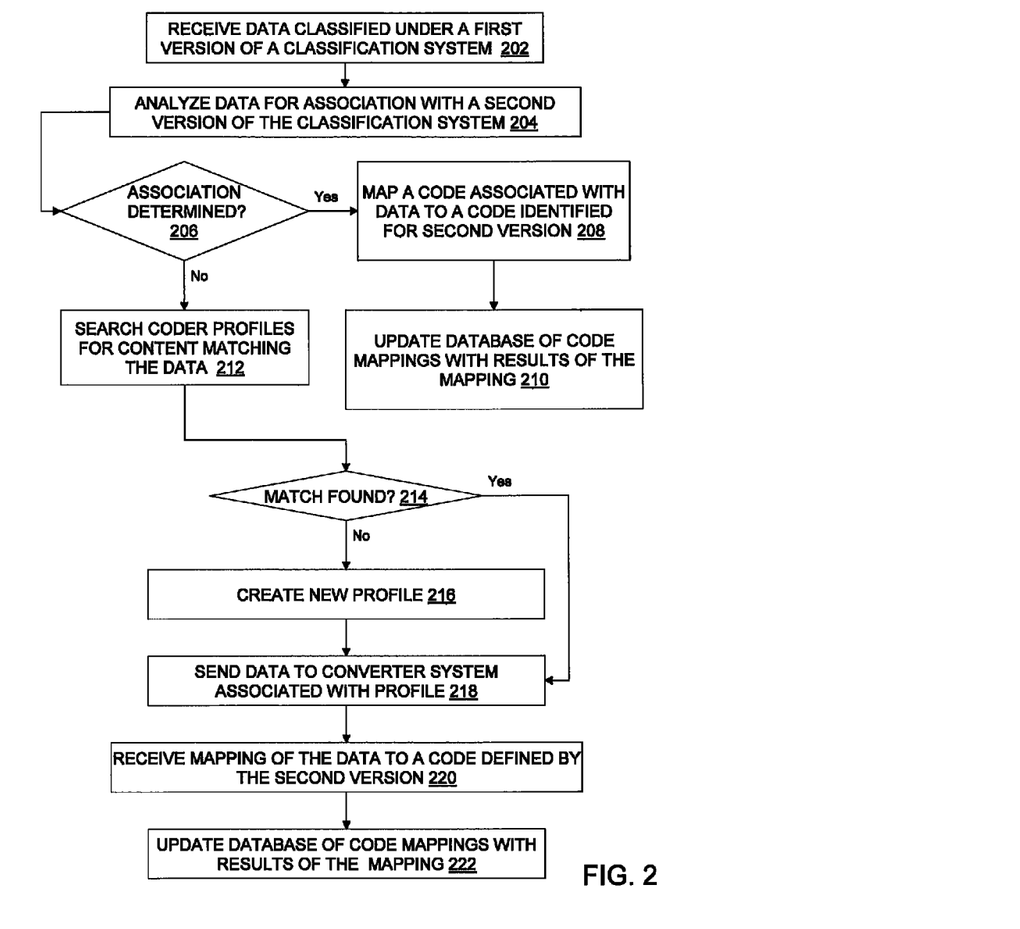
FIG. 2 is a flow diagram illustrating a process for training the system to resolve codes between code versions and for determining a profile assignment for any unresolved codes in accordance with an embodiment.

Turning now to FIG. 2, a process for training the system to resolve codes between code versions of a classification system and for determining a profile assignment for unresolved codes will now be described in an exemplary embodiment. As indicated above, an insurer operating one version of a classification system may not readily recognize the codes presented in a claim form that comply with a different version of the classification system. The process of FIG. 2 assumes that a claim form has been received at the host system computer 102.

At block 202, the training component 111 receives data (e.g., a claim form) classified with a code defined by a version of a classification system (e.g., ICD-10). The data may include a medical condition and/or other description of a diagnosis, procedure, or related service.

Figure 4:
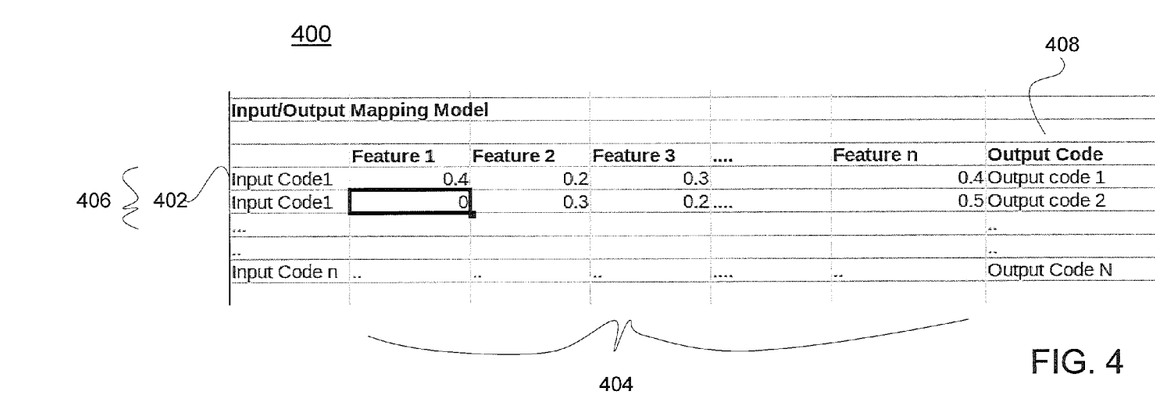
FIG. 4 is a model with sample data used in mapping codes between versions of the classification system in accordance with an embodiment.

At block 204, the training component 111 analyzes the data to determine an association between the code in the claim form and a code defined by a different version of the classification system stored in the storage device 104. In one embodiment, the training component 111 parses the data, and selects primary terms from the data. For example, a claim form indicating a medical condition of diabetes may include symptoms, such as blurry vision, excess thirst, and fatigue. The model 400 shown in FIG. 4 depicts a code 402 from the first version (V-A), which has been input to the model 400. The parsed data from the claim form is shown as Features 1-n in columns 404. Values shown in these columns 404 reflect a corresponding score or relevance value determined by the training component 111. As shown in FIG. 4, there are two instances 406 of Input Code1. These instances represent a one-to-many mapping scenario in which a single input code may be mapped to two different output codes (i.e., codes from version V-B) shown, e.g., in column 408. As shown in FIG. 4, the relevance values shown in columns 404 determine which of the characteristics associated with the output codes most closely relate to the characteristics of the data in the claim form.

At block 206, the training component 111 determines whether an association exists (e.g., whether a corresponding code from the second version may be mapped to the code in the claim form). If so, the training component 111 maps the code associated with the data to a code identified for the second version of the classification system at block 208. The code mappings database is updated to reflect the mapping between the codes at block 210.

Figure 5:
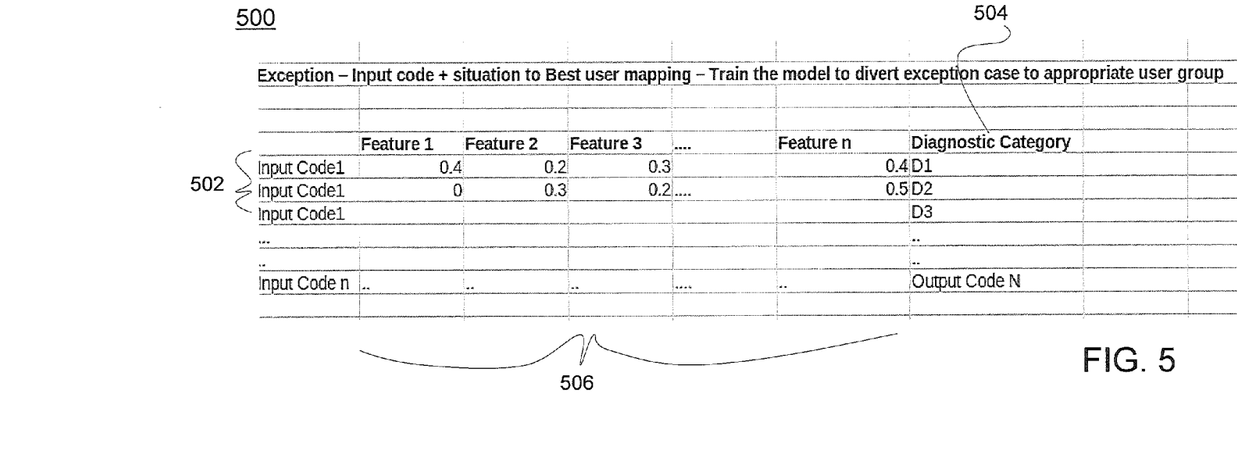
FIG. 5 is a model with sample data used in determining coder assignments in accordance with an embodiment.

If, however, at block 206, the training component 111 is unable to determine an association for the data, the profiler component 114 is notified, and the profiler component 114 searches the storage device 116 for content matching at least a portion of the data, such as the primary terms determined from the analysis at block 212. Alternatively, the profiler component 114 may determine from the training component 111 a subject area associated with the claim form. The profiler component 114 may then search the storage device 116 for profiles in which a high proficiency for the subject area is indicated. FIG. 5 illustrates a model 500 with sample data used in determining assignments of claim forms to coders. As shown in FIG. 5, one code 502 (i.e., Input Code1) has been associated with three possible diagnostic categories (D1, D2, and D3) shown in column 504. The training component 111 utilizes scores or relevance values 506 assigned to features from claim forms previously processed by the training component 111. In previously conducted processing for the code, there have been three different diagnostic categories or subject matter areas deemed to be relevant to the respective claim forms. Based on the relevancy scores, the training component 111 selects a corresponding diagnostic category.

At block 214, the profiler component 114 determines whether a match is found in response to the search. If no match is found, this means that there is currently no experienced coder associated with this data. In this event, the profiler component 114 may be configured to create a new profile at block 216. The new profile may be assigned to a new coder or to an existing coder who has the capacity to take on additional work.

Otherwise, if a match is found at block 214, or alternatively, once the new profile has been created at block 216, the profiler component 114 sends the data to a converter system associated with the coder having the profile at block 218. In this manner, coders known to be proficient in a particular subject area are assigned to incoming claims relating to that subject area, thereby streamlining the conversion mapping between classification systems.

The coder processes the data to convert the code received in the data to a corresponding code of the classification system stored in the storage device 104 (i.e., the pre-conversion database) at block 220. The conversion includes mapping the code from the data to another code that is defined by a different classification system. The coder sends the results of the mapping to the code mapping database for updating.

At block 222, the profiler component 114 updates the code mapping database in the storage device 104 to reflect the results of the mapping performed by the coder.

It will be understood that the mapping between codes of two versions of a classification system is not limited to a one-to-one mapping but may extend to a one-to-many mapping, a many-to-one mapping, and/or no mapping. For example, a one-to-many mapping may exist when a single code for a first version of the classification system applies to multiple codes of the second version of the classification system.

Figure 3:
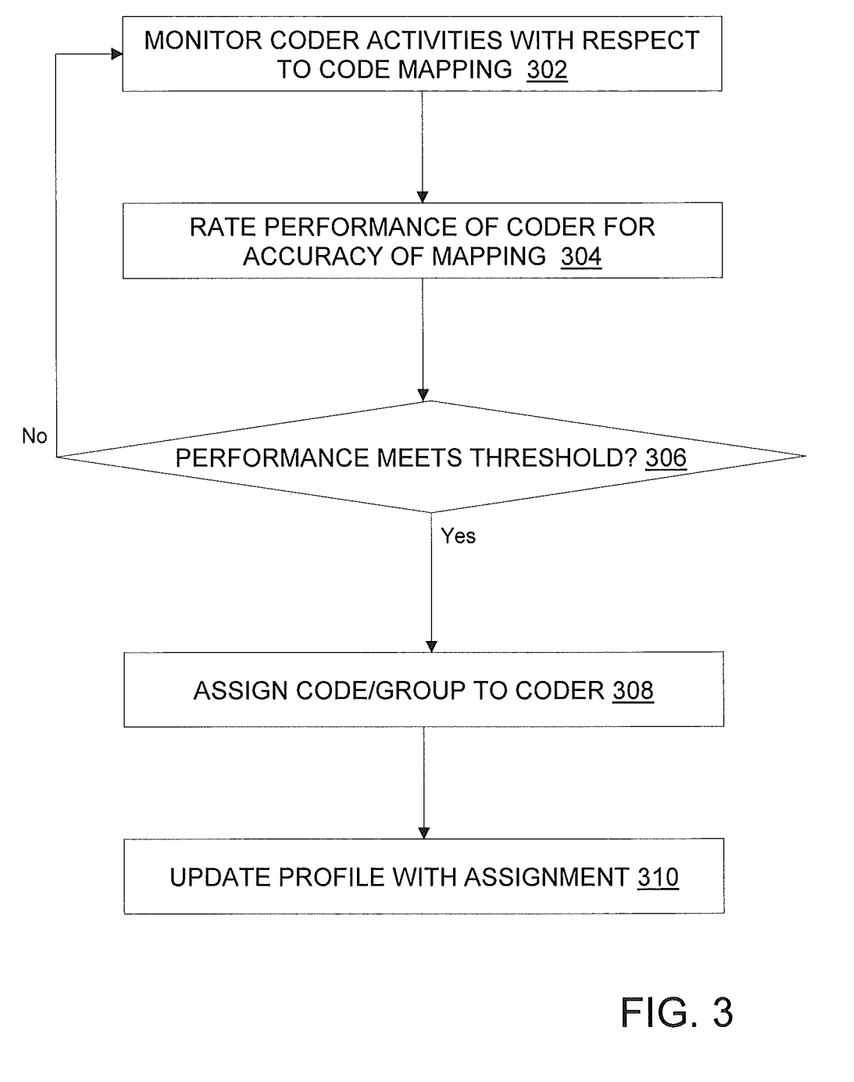
FIG. 3 is a flow diagram illustrating a process for qualifying a coder to perform a code mapping process in accordance with an embodiment.

As indicated above, the exemplary intelligent delegation of codes for conversion mapping between classification systems provides the ability to monitor a coder's performance with respect to various subject areas in which claims have been processed by the coder and rate the coder with a proficiency rating in order to determine which in subject areas future assignments should be relegated for the coder. Turning now to FIG. 3, process for qualifying a coder for conversion mapping with respect to a body of information will now be described in an exemplary embodiment.

Figure 6:
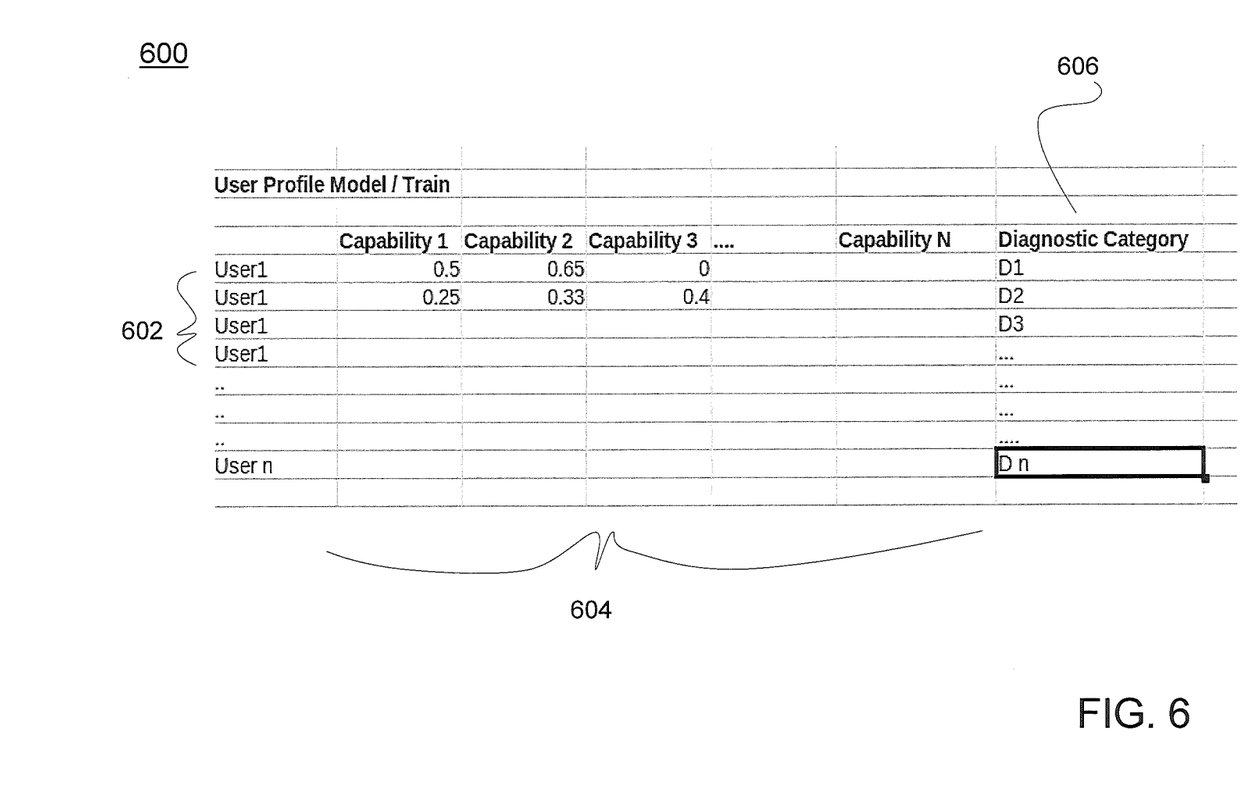
FIG. 6 depicts a coder profile with sample data in accordance with an embodiment.

At block 302, the profiler component 114 monitors coder activities in terms of the accuracy in which the coder has resolved codes between versions of a classification system with respect to a particular subject area. The profiler component 114 may determine accuracy, e.g., by auditing a number of code mappings performed by the coder and verifying that the mapping reflects the most relevant relationship (e.g., using key word searching of the descriptions associated with the codes) between codes of two different versions of the classification system at block 304. The profiler component 114 may be configured with a threshold measure of accuracy, e.g., capability scores associated with mappings for a particular subject area (e.g., conditions/procedures associated with diabetes). As shown in FIG. 6, a profile 600 including sample data used in evaluating a coder is accessed by the profiler component 114. The profile identifies a coder (i.e., User1) 602 along with capabilities 604 of the coder. The capabilities 604 reflect scores indicating the coder's proficiency for an associated subject matter area (e.g., diagnostic category 606). A coder with a high overall score indicates the coder is highly proficient in accurately mapping codes associated with the diagnostic area to codes for the second version of the classification system.

At block 306, the profiler component 114 determines whether the coder's conversion mappings are accurate within the threshold value. If so, the coder is assigned a subject area at block 308 and the coder's profile is updated to reflect this proficiency at block 310. Future incoming and unresolved claims for this subject area may not be automatically assigned to this coder.

In an embodiment, a converter system having a first profile that corresponds to code version V-A and a converter system having a second profile that corresponds to code version V-B may be accessed by a converter system configured to map code version V-A to code version V-B based on the trained model as described above. Alignment between code versions V-A and V-B are based on one or more hyperplanes (shown generally in the Figures). A converter system transfers code version V-A to an appropriate exception queue based on the trained model, and alignment between the code version and the exception queue may also be based on one or more hyperplanes, as shown generally in the Figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, blocks, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or schematic diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

As described above, embodiments can be embodied in the form of computer-implemented processes and apparatuses for practicing those processes. In embodiments, the invention is embodied in computer program code executed by one or more network elements. Embodiments include a computer program product on a computer usable medium with computer program code logic containing instructions embodied in tangible media as an article of manufacture. Exemplary articles of manufacture for computer usable medium may include floppy diskettes, CD-ROMs, hard drives, universal serial bus (USB) flash drives, or any other computer-readable storage medium, wherein, when the computer program code logic is loaded into and executed by a computer, the computer becomes an apparatus for practicing the invention. Embodiments include computer program code logic, for example, whether stored in a storage medium, loaded into and/or executed by a computer, or transmitted over some transmission medium, such as over electrical wiring or cabling, through fiber optics, or via electromagnetic radiation, wherein, when the computer program code logic is loaded into and executed by a computer, the computer becomes an apparatus for practicing the invention. When implemented on a general-purpose microprocessor, the computer program code logic segments configure the microprocessor to create specific logic circuits.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A system, comprising:
   a computer processor; and
   an application executable by the computer processor, the application configured to implement a method, the method comprising:
   receiving data that is classified with a first code, the first code defined by a first version of a classification system, the first code to be re-classified to a second code that is defined by a second version of the classification system;
   searching a database of profiles for content that matches at least a portion of the data;
   sending the data to a converter system having one of the profiles that is associated with the content responsive to the searching;
   receiving, from the converter system, a mapping of the first code to the second code;
   updating a database of codes with results of the mapping;
   analyzing, over a duration of time, mapping activities performed by a coder via the converter system, the mapping activities including mapping of codes between the first version of the classification system and the second version of the classification system;
   determining an accuracy level of the mapping activities with respect to the coder; and updating a profile of the coder, based on the accuracy level, to include a proficiency of the coder with respect to a subject matter area that relates to the data.

2. The system of claim 1, wherein the data is indicative of a medical condition, treatment performed, and medical symptom.

3. The system claim 2, wherein the first version of the classification system is a first version of a diagnostic and procedure codes index that is updated from a second version of the diagnostic and procedure codes index, the second version of the diagnostic and procedure codes index corresponding to the second version of the classification system.

4. The system of claim 2, wherein the data is received by the computer processor on a medical claim form.

5. The system of claim 1, wherein the mapping of the first code also includes a mapping of the first code to a third code defined by the second version of the classification system.

6. A computer program product comprising a non-transitory storage medium having instructions embodied thereon, which when executed by a computer processor, causes the computer processor to implement a method, the method comprising:
 receiving data that is classified with a first code, the first code defined by a first version of a classification system, the first code to be re-classified to a second code that is defined by a second version of the classification system;
 searching a database of profiles for content that matches at least a portion of the data;
 sending the data to a converter system having one of the profiles that is associated with the content responsive to the searching;
 receiving, from the converter system, a mapping of the first code to the second code;
 updating a database of codes with results of the mapping;
 analyzing, over a duration of time, mapping activities performed by a coder via the converter system, the mapping activities including mapping of codes between the first version of the classification system and the second version of the classification system;
 determining an accuracy level of the mapping activities with respect to the coder; and
 updating a profile of the coder, based on the accuracy level, to include a proficiency of the coder with respect to a subject matter area that relates to the data.

7. The computer program product of claim 6, wherein the data is indicative of at least one of a medical condition, treatment performed, and medical symptom.

8. The computer program product of claim 7, wherein the first version of the classification system is a first version of a diagnostic and procedure codes index that is updated from a second version of the diagnostic and procedure codes index, the second version of the diagnostic and procedure codes index corresponding to the second version of the classification system.

9. The computer program product of claim 7, wherein the data is received on a medical claim form.

10. The computer program product claim 6, wherein the mapping of the first code further includes a mapping of the first code to a third code defined by the second version of the classification system.

11. The computer program product of claim 6, wherein the mapping of the first code further includes a mapping of multiple codes defined by the first version of the classification system to the second code defined by the second version of the classification system.

* * * * *